United States Patent
Thomas

(10) Patent No.: US 9,181,562 B2
(45) Date of Patent: Nov. 10, 2015

(54) SOYBEAN VARIETY DLL1273

(71) Applicant: BAYER CROPSCIENCE LP, Research Triangle Park, NC (US)

(72) Inventor: James D Thomas, DeWitt, AR (US)

(73) Assignee: BAYER CROPSCIENCE LP, Research Triangle Park, NC (US)

( * ) Notice: Subject to any disclaimer, the term of this patent is extended or adjusted under 35 U.S.C. 154(b) by 0 days.

(21) Appl. No.: 13/832,366

(22) Filed: Mar. 15, 2013

(65) Prior Publication Data

US 2013/0205435 A1 Aug. 8, 2013

(51) Int. Cl.
*A01H 5/10* (2006.01)
*C12N 15/82* (2006.01)

(52) U.S. Cl.
CPC .............. *C12N 15/8274* (2013.01); *A01H 5/10* (2013.01); *C12N 15/8245* (2013.01); *C12N 15/8246* (2013.01); *C12N 15/8247* (2013.01); *C12N 15/8275* (2013.01); *C12N 15/8277* (2013.01); *C12N 15/8278* (2013.01); *C12N 15/8279* (2013.01); *C12N 15/8286* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,850,009 A | 12/1998 | Kevern | |
| 5,968,830 A | 10/1999 | Dan et al. | |
| 6,965,061 B2 | 11/2005 | Shannon | |

OTHER PUBLICATIONS

Eshed, et al., 1996, "Less-than-additive epistatic interactions of quantitative trait loci in tomato". Genetics 143: 1807-1817.
Goldman, et al., 1994, "Molecular Markers Associated with Maize Kernel Oil Concentration in an Illinois High Protein × Illinois Low Protein Cross" Crop Sci. 34: 908-915.
Kraft, et al., 2000, "Linkage disequilibrium and fingerprinting in sugar beet", Theor. App. Genet. 101:323-326.
Narvel, et al., 2001, "A Retrospective DNA Marker Assessment of the Development of Insect Resistant Soybean", Crop Sci, 41:1931-1939.
Poehlman, J.M. and Sleper, D.A., "Methods in Plant Breeding, in Breeding Field Crops", 4th ed. (1995), Iowa State University Press, pp. 172-174.
Willmot, et al., 1989 "Genetic analysis of brown stem rot resistance in soybean", Crop Sci. 29: 672-674.
US PVP, Certificate No. 009800152, Granted Application of Hornbeck Seed Co., Inc., Jul. 19, 2002.

*Primary Examiner* — Brent T Page

(57) ABSTRACT

The soybean variety DLL1273 is disclosed. The invention relates to seeds, plants, plant cells, plant tissue, harvested products and soybean lint as well as to hybrid soybean plants and seeds obtained by repeatedly crossing plants of variety DLL1273 with other plants. The invention also relates to plants and varieties produced by the method of essential derivation from plants of DLL1273 and to plants of DLL1273 reproduced by vegetative methods, including but not limited to tissue culture of regenerable cells or tissue from DLL1273.

25 Claims, No Drawings

SOYBEAN VARIETY DLL1273

FIELD OF THE INVENTION

This invention relates to the field of plant breeding. More particularly, the invention relates to a variety of soybean designated as DLL1273, its essentially derived varieties and the hybrid varieties obtained by crossing DLL1273 as a parent line with plants of other varieties or parent lines.

BACKGROUND OF THE INVENTION

Soybean, *Glycine max* (L), is an important and valuable field crop. Thus, a continuing goal of soybean plant breeders is to develop stable, high yielding soybean varieties that are agronomically sound. The reasons for this goal are obviously to maximize the amount of grain produced on the land used and to supply food for both animals and humans. To accomplish this goal, the soybean breeder must select and develop soybean plants that have traits that result in superior varieties.

Due to the environment, the complexity of the structure of genes and location of a gene in the genome, among other factors, it is difficult to predict the phenotypic expression of a particular genotype. In addition, a plant breeder may only apply his skills on the phenotype and not, or in a very limited way, on the level of the genotype. As a result, a particular plant breeder cannot breed the same variety twice using the same parents and the same methodology. Thus, a newly bred variety is an unexpected result of the breeding process. Indeed, each variety contains a unique combination of characteristics.

By carefully choosing the breeding parents, the breeding and selection methods, the testing layout and testing locations, the breeder may breed a particular variety type. In addition, a new variety may be tested in special comparative trials with other existing varieties in order to determine whether the new variety meets the required expectations.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a new soybean variety designated DLL1273. This invention thus relates to the seeds of soybean variety DLL1273, to the plants of soybean variety DLL1273 and to methods for producing a soybean plant produced by crossing soybean variety DLL1273 with itself or another soybean variety, and the creation of variants by mutagenesis or transformation of soybean variety DLL1273.

Thus, any such methods using the soybean variety DLL1273 are part of this invention: selfing, backcrosses, hybrid production, crosses to populations, and the like. All plants produced using soybean variety DLL1273 as at least one parent are within the scope of this invention. Advantageously, this soybean variety could be used in crosses with other, different, soybean plants to produce first generation ($F_1$) soybean hybrid seeds and plants with superior characteristics.

In another aspect, the present invention provides for single or multiple gene converted plants of soybean variety DLL1273. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, and industrial usage. The gene may be a naturally occurring soybean gene or a transgene introduced through genetic engineering techniques.

In another aspect, the present invention provides regenerable cells for use in tissue culture of soybean plant DLL1273. The tissue culture will preferably be capable of regenerating plants having all the physiological and morphological characteristics of the foregoing soybean plant, and of regenerating plants having substantially the same genotype as the foregoing soybean plant. Preferably, the regenerable cells in such tissue cultures will be embryos, protoplasts, meristematic cells, callus, pollen, leaves, anthers, cotyledons, hypocotyl, pistils, roots, root tips, flowers, seeds, petiole, pods or stems. Still further, the present invention provides soybean plants regenerated from the tissue cultures of the invention.

In addition to the exemplary aspects and embodiments described above, further aspects and embodiments will become apparent by study of the following descriptions.

DETAILED DESCRIPTION OF THE INVENTION

The present invention relates to soybean variety DLL1273. The variety has shown uniformity and stability, as described in the following variety description information. It has been self-pollinated a sufficient number of generations with careful attention to uniformity of plant type. The line has been increased with continued observation for uniformity.

Soybean variety DLL1273 contains a transgene of event LL55, which confers resistance to LIBERTY® (active ingredient glufosinate-ammonium) herbicide. Soybean variety DLL1273 was derived from a cross of an LL55 donor parent and the conventional variety HBK C4926.

Soybean variety DLL1273 has the following morphologic and other characteristics:

TABLE 1

| PARAMETER | VALUE |
| --- | --- |
| Average Yield (bushels per acre) | 65.55 |
| Percentage of check variety | 97.2 |
| Average days to maturity | 279 |
| flower color | white |
| plant habit | determinate |
| pubescence color | tawny |
| pod color | tawny |
| plant height (inches) | |
| lodging resistance | 2.5 |
| hilum color | light brown |
| phythoptera root rot | susceptible to race 1 |
| sudden death syndrome | |
| stem canker (2011) | resistant |
| stem canker (2012) | resistant |
| frogeye leaf spot | 4.5 |
| Soybean cyst nematode resistance at reproductive stage R3 | highly resistant |
| Soybean cyst nematode resistance at reproductive stage R5 | highly resistant |

TABLE 1-continued

| PARAMETER | VALUE |
|---|---|
| Soybean cyst nematode reproduction of females on indicator lines* | 7 |
| SCN source | PEKING |
| root knot nematode resistance | |
| Salt | no apparent chlorosis |

*Soybean indicator lines:
0 = no reproduction over 100% of the indicator lines
1 = reproduction on Peking
2 = reproduction on PI88788
3 = reproduction on PI90763
4 = reproduction on PI437654
5 = reproduction on PI209332
6 = reproduction on PI89772
7 = reproduction on Cloud This invention is also directed to methods for producing a soybean plant by crossing a first parent soybean plant with a second parent soybean plant, wherein the first or second soybean plant is the soybean plant from soybean variety DLL1273. Further, both first and second parent soybean plants may be from soybean variety DLL1273. Therefore, any methods using soybean variety DLL1273 are part of this invention: selfing, backcrosses, hybrid breeding, and crosses to populations. Any plants produced using soybean variety DLL1273 as at least one parent are within the scope of this invention.

Additional methods include but are not limited to expression vectors introduced into plant tissues using a direct gene transfer method such as microprojectile-mediated delivery, DNA injection, electroporation and the like. More preferably expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last twenty years several methods for producing transgenic plants have been developed and the present invention, in particular embodiments, also relates to transformed versions of the claimed variety or line.

Plant transformation involves the construction of an expression vector which will function in plant cells. Such a vector comprises DNA comprising a gene under the control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed soybean plants using transformation methods as described below to incorporate transgenes into the genetic material of the soybean plant(s).

Expression Vectors for Soybean Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. USA, 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986)). Other selectable marker genes confer resistance to herbicides such as glyphosate, glufosinate, bromoxynil, or HPPD inhibitors (Comai et al., Nature 317:741-744 (1985); Gordon-Kamm et al., Plant Cell 2:603-618 (1990); Stalker et al., Science 242:419-423 (1988); and U.S Patent Publication 20120311743).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., Science 233:478 (1986), Charest et al., Plant Cell Rep. 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., Plant Mol. Biol. Rep. 5:387 (1987), Teeri et al., EMBO J. 8:343 (1989), Koncz et al., Proc. Natl. Acad. Sci. USA 84:131 (1987), DeBlock et al., EMBO J. 3:1681 (1984)).

Further, a gene encoding Green Fluorescent Protein (GFP) can be utilized as a marker for gene expression in prokaryotic and eukaryotic cells (Chalfie et al., Science 263:802 (1994)). GFP and mutants of GFP may be used as screenable markers.

Expression Vectors for Soybean Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., Proc. Natl. Acad. Sci. U.S.A. 90:4567-4571 (1993)); In2 gene from maize which responds to benzenesulfonamide herbicide safeners (Hershey et al., Mol. Gen. Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. USA 88:0421 (1991)).

B. Constitutive Promoters—A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is a soybean plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. In various embodiments, the soybean plant of the invention further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families, through the Cry72 families; etc., or any of the toxins listed on Crickmore et al. (2003) "*Bacillus thuringiensis* toxin nomenclature," at www.biols.susx.ac.uk/Home/Neil_Crickmore/Bt/index). It will be understood by one of skill in the art that the transgenic plant may comprise any gene imparting an agronomic trait of interest. Additional genes implicated in this regard include, but are not limited to, those referenced in the patent publications listed in Table 2, each of which is incorporated by reference in its entirety:

TABLE 2

| Trait | Reference |
| --- | --- |
| Water use efficiency | WO 2000/073475 |
| | WO2009/150541 |
| | WO2009/150541 |
| | WO2012075429 |
| | WO2012077020 |
| Nitrogen use efficiency | WO 1995/009911 |
| | WO 1997/030163 |
| | WO 2007/092704 |
| | WO 2007/076115 |
| | WO 2005/103270 |
| | WO 2002/002776 |
| | WO2008/051608 |
| | WO2008/112613 |
| | WO2009/015096 |
| | WO2009/061776 |
| | WO2009/105492 |
| | WO2009/105612 |
| | WO2009/117853 |
| | WO2010/006010 |
| | WO2009/117853 |
| | WO2009/061776 |
| | WO2009/015096 |
| | WO2009/105492 |
| | WO2009/105612 |
| | WO 2010/053621 |
| | WO 2010/053867 |
| | WO2010/077890 |
| | WO 2010/086220 |
| | WO 2010/111568 |
| | WO 2010/140388 |
| | WO2010/007496 |
| | WO2011/022597 |
| | WO2011/022608 |
| | WO2012087140 |
| Improved photosynthesis | WO 2008/056915 |
| | WO 2004/101751 |
| Nematode resistance | WO 1995/020669 |
| | WO 2001/051627 |
| | WO 2008/139334 |
| | WO 2008/095972 |
| | WO 2006/085966 |
| | WO 2003/033651 |
| | WO 1999/060141 |
| | WO 1998/012335 |
| | WO 1996/030517 |
| | WO 1993/018170 |
| | WO2008/095886 |

TABLE 2-continued

| Trait | Reference |
| --- | --- |
| | WO2008/095887 |
| | WO2008/095888 |
| | WO2008/095889 |
| | WO2008/095910 |
| | WO2008/095911 |
| | WO2008/095916 |
| | WO2008/095919 |
| | WO2008/095969 |
| | WO2008/095970 |
| | WO2008/095972 |
| | WO2008/110522 |
| | WO2008/139334 |
| | WO2008/152008 |
| | WO2010/077858 |
| | WO 2010/091230 |
| | WO 2010/102172 |
| | WO 2010/106163 |
| | WO2011/082217 |
| | WO2011/003783 |
| Reduced pod dehiscence | WO 2006/009649 |
| | WO 2004/113542 |
| | WO 1999/015680 |
| | WO 1999/000502 |
| | WO 1997/013865 |
| | WO 1996/030529 |
| | WO 1994/023043 |
| Aphid resistance | WO 2006/125065 |
| | WO 1997/046080 |
| | WO 2008/067043 |
| | WO 2004/072109 |
| | WO2009/091860 |
| | WO2010036764 |
| *Sclerotinia* resistance | WO 2006/135717 |
| | WO 2006/055851 |
| | WO 2005/090578 |
| | WO 2005/000007 |
| | WO 2002/099385 |
| | WO 2002/061043 |
| *Bremia* resistance | US 20070022496 |
| | WO 2000/063432 |
| | WO 2004/049786 |
| | WO2009/111627 |
| | WO2009/111627 |
| *Erwinia* resistance | WO 2004/049786 |
| Closterovirus resistance | WO 2007/073167 |
| | WO 2007/053015 |
| | WO 2002/022836 |
| Stress tolerance (including drought tolerance) | WO 2010/019838 |
| | WO 2009/049110 |
| | WO2008/002480 |
| | WO2005/033318 |
| | WO2008/002480 |
| | WO2008/005210 |
| | WO2008/006033 |
| | WO2008/008779 |
| | WO2008/022486 |
| | WO2008/025097 |
| | WO2008/027534 |
| | WO2008/027540 |
| | WO2008/037902 |
| | WO2008/046069 |
| | WO2008/053487 |
| | WO2008/057642 |
| | WO2008/061240 |
| | WO2008/064222 |
| | WO2008/064341 |
| | WO2008/073617 |
| | WO2008/074025 |
| | WO2008/076844 |
| | WO2008/096138 |
| | WO2008/110848 |
| | WO2008/116829 |
| | WO2008/117537 |
| | WO2008/121320 |
| | WO2008/125245 |
| | WO2008/142034 |
| | WO2008/142036 |
| | WO2008/150165 |

TABLE 2-continued

| Trait | Reference |
|---|---|
| | WO2008/092935 |
| | WO2008/145675 |
| | WO2009/010460 |
| | WO2009/016240 |
| | WO2009/031664 |
| | WO2009/038581 |
| | WO2009/049110 |
| | WO2009/053511 |
| | WO2009/054735 |
| | WO2009/067580 |
| | WO2009/073605 |
| | WO2009/077611 |
| | WO2009/079508 |
| | WO2009/079529 |
| | WO2009/083958 |
| | WO2009/086229 |
| | WO2009/092009 |
| | WO2009/094401 |
| | WO2009/094527 |
| | WO2009/102965 |
| | WO2009/114733 |
| | WO2009/117448 |
| | WO2009/126359 |
| | WO2009/126462 |
| | WO2009/129162 |
| | WO2009/132057 |
| | WO2009/141824 |
| | WO2009/148330 |
| | WO 2010/055024 |
| | WO 2010/058428 |
| | WO 2010/064934 |
| | WO2010/076756 |
| | WO 2010/083178 |
| | WO 2010/086221 |
| | WO 2010/086277 |
| | WO 2010/101818 |
| | WO 2010/104848 |
| | WO 2010/118338 |
| | WO 2010/120017 |
| | WO 2010/120054 |
| | WO 2010/121316 |
| | WO 2010/127579 |
| | WO 2010/134654 |
| | WO 2010/139993 |
| | WO2010/039750 |
| | WO2011/034968 |
| | WO2011/001286 |
| | WO2011/017492 |
| | WO2011/018662 |
| | WO2011/024065 |
| | WO2011/038389 |
| | WO2011/46772 |
| | WO2011/053897 |
| | WO2011/052169 |
| | WO2011/063706 |
| | WO2011/067745 |
| | WO2011/079277 |
| | WO2011/080674 |
| | WO2011/083290 |
| | WO2011/083298 |
| | WO2011/091764 |
| | WO2011/052169 |
| | WO2011/053897 |
| | WO2011/056769 |
| | WO2011/063706 |
| | WO2011/067745 |
| | WO2011/083290 |
| | WO2011/083298 |
| | WO2011/091764 |
| | WO2011/096609 |
| | WO2011/122761 |
| Tobamovirus resistance | WO 2006/038794 |
| | WO2009086850 |
| Yield | WO 2010/046221 |
| | WO 2010/046471 |
| | WO 2010/049897 |
| | WO 2010/055837 |
| | WO 2010/065867 |

TABLE 2-continued

| Trait | Reference |
|---|---|
| | WO2010/069847 |
| | WO2010/075143 |
| | WO2010/075243 |
| | WO 2010/100595 |
| | WO 2010/102220 |
| | WO 2010/104092 |
| | WO 2010/108836 |
| | WO 2010/120862 |
| | WO 2010/123667 |
| | WO 2010/124953 |
| | WO 2010/125036 |
| | WO 2010/127969 |
| | WO 2010/129501 |
| | WO 2010/140388 |
| | WO 2010/140672 |
| | WO2011/011273 |
| | WO2011/000466 |
| | WO2011/003800 |
| | WO2011/006717 |
| | WO2011/008510 |
| | WO2011/009801 |
| | WO2011/011412 |
| | WO2011/015985 |
| | WO2011/020746 |
| | WO2011/021190 |
| | WO2011/025514 |
| | WO2011/025515 |
| | WO2011/025516 |
| | WO2011/025840 |
| | WO2011/031680 |
| | WO2011/036160 |
| | WO2011/036232 |
| | WO2011/041796 |
| | WO2011/044254 |
| | WO2011/048009 |
| | WO2011/053898 |
| | WO2011/051120 |
| | WO2011/058029 |
| | WO2011/061656 |
| | WO2011/085062 |
| | WO2011/088065 |
| | WO2011/053898 |
| | WO2011/058029 |
| | WO2011/061656 |
| | WO2011/085062 |
| | WO2011/088065 |
| | WO2011/095958 |
| | WO2011/097215 |
| | WO2011/099006 |
| | WO2011/104128 |
| | WO2011/104141 |
| | WO2011/104143 |
| | WO2011/104155 |
| | WO2011/106734 |
| | WO2011/106794 |
| | WO2011/109661 |
| | WO2011/114279 |
| | WO2011/114305 |
| | WO2011/114312 |
| | WO2011/114313 |
| | WO2011/117800 |
| | WO2011/135527 |
| | WO2011/136909 |
| | WO2011/139431 |
| | WO2011/140329 |
| | WO2011/146754 |
| | WO2011/147826 |
| | WO2011/157976 |
| | WO2011/161617 |
| | WO2011/161620 |
| | WO2011/109618 |
| | WO2011/159452 |
| | WO2012078949 |
| | WO2012083219 |
| | WO2012084742 |
| | WO2012084756 |
| | WO2012087903 |
| | WO2012087940 |

TABLE 2-continued

| Trait | Reference |
|---|---|
| | WO2012090500 |
| | WO2012091939 |
| | WO2012092106 |
| | WO2012092327 |
| | WO2012092573 |
| | WO2012092580 |
| | WO2012092596 |
| | WO2012093032 |
| | WO2012093833 |
| | WO2012097720 |
| | WO2012098517 |
| | WO2012102999 |
| | WO2012106321 |
| Oil content/composition | WO 2010/045324 |
| | WO 2010/053541 |
| | WO 2010/130725 |
| | WO 2010/140682 |
| | WO2011/006948 |
| | WO2011/049627 |
| | WO2011/060946 |
| | WO2011/062748 |
| | WO2011/064181 |
| | WO2011/064183 |
| | WO2011/075716 |
| | WO2011/079005 |
| | WO2011/049627 |
| | WO2011/062748 |
| | WO2011/064181 |
| | WO2011/064183 |
| | WO2011/079005 |
| | WO2011/146524 |
| | WO2011/161093 |
| | WO2011/163557 |
| | WO2011/163632 |
| | WO2011/163632 |
| | WO2012074385 |
| | WO2012074386 |
| | WO2012103452 |
| Biopharmaceutical production | WO 2010/121818 |
| | WO2011/119115 |
| Improved recombination | WO2010/071418 |
| | WO 2010/133616 |
| plant appearance | WO 2010/069004 |
| | WO2011/060552 |
| Disease control (other) | WO 2010/059558 |
| | WO2010/075352 |
| | WO2010/075498 |
| | WO 2010/085289 |
| | WO 2010/085295 |
| | WO 2010/085373 |
| | WO2009/000736 |
| | WO2009/065863 |
| | WO2009/112505 |
| | WO 2010/089374 |
| | WO 2010/120452 |
| | WO 2010/123904 |
| | WO 2010/135782 |
| | WO2011/025860 |
| | WO2011/041256 |
| | WO2011/031006 |
| | WO2011/031922 |
| | WO2011/075584 |
| | WO2011/075585 |
| | WO2011/075586 |
| | WO2011/075587 |
| | WO2011/075588 |
| | WO2011/084622 |
| | WO2011/084626 |
| | WO2011/084627 |
| | WO2011/084629 |
| | WO2011/084630 |
| | WO2011/084631 |
| | WO2011/084314 |
| | WO2011/084324 |
| | WO2011/023571 |
| | WO2011/040880 |
| | WO2011/082304 |
| | WO2011/003783 |
| | WO2011/020797 |
| | WO2011/069953 |
| | WO2011/075584 |
| | WO2011/075585 |
| | WO2011/075586 |
| | WO2011/075587 |
| | WO2011/075588 |
| | WO2011/084314 |
| | WO2011/084324 |
| | WO2011/084622 |
| | WO2011/084626 |
| | WO2011/084627 |
| | WO2011/084629 |
| | WO2011/084630 |
| | WO2011/084631 |
| | WO2011/133892 |
| | WO2011/133895 |
| | WO2011/133896 |
| | WO2011/082217 |
| | WO2011/104153 |
| | WO2011/082304 |
| | WO2011/100650 |
| | WO2011/158242 |
| | WO2012003207 |
| | WO2012004013 |
| | WO2012004401 |
| | WO2012006271 |
| | WO2012006426 |
| | WO2012006439 |
| | WO2012006443 |
| | WO2012006622 |
| | WO2012007916 |
| | WO2012007919 |
| | WO2012009551 |
| | WO2012011034 |
| | WO2012012403 |
| | WO2012015039 |
| | WO2012058266 |
| | WO2012058458 |
| | WO2012058528 |
| | WO2012058730 |
| | WO2012061513 |
| | WO2012063200 |
| | WO2012065166 |
| | WO2012065219 |
| | WO2012066008 |
| | WO2012067127 |
| | WO2012068966 |
| | WO2012071039 |
| | WO2012071040 |
| Herbicide tolerance | U.S. Pat. No. 4,761,373 |
| | U.S. Pat. No. 5,304,732 |
| | U.S. Pat. No. 5,331,107 |
| | U.S. Pat. No. 5,718,079 |
| | U.S. Pat. No. 6,211,438 |
| | U.S. Pat. No. 6,211,439 |
| | U.S. Pat. No. 6,222,100 |
| | US 2003/0217381 |
| | US 2003/0217381 |
| | WO2004/106529 |
| | WO2000/27182 |
| | WO2005/20673 |
| | WO 2001/85970 |
| | U.S. Pat. No. 5,545,822 |
| | U.S. Pat. No. 5,736,629 |
| | U.S. Pat. No. 5,773,703, |
| | U.S. Pat. No. 5,773,704 |
| | U.S. Pat. No. 5,952,553 |
| | U.S. Pat. No. 6,274,796 |
| | WO 2004/106529 |
| | WO2004/16073 |
| | WO 2003/14357 |
| | WO 2003/13225 |
| | WO 2003/14356 |
| | U.S. Pat. No. 5,188,642 |
| | U.S. Pat. No. 4,940,835 |
| | U.S. Pat. No. 5,633,435 |
| | U.S. Pat. No. 5,804,425 |

TABLE 2-continued

| Trait | Reference |
|---|---|
| | U.S. Pat. No. 5,627,061. |
| | U.S. Pat. No. 5,646,024 |
| | U.S. Pat. No. 5,561,236 |
| | U.S. Pat. No. 6,333,449 |
| | U.S. Pat. No. 6,933,111 |
| | U.S. Pat. No. 6,468,747. |
| | U.S. Pat. No. 6,376,754 |
| | U.S. Pat. No. 7,105,724 |
| | U.S. Pat. No. 7,105,724 |
| | WO 2008/051633 |
| | U.S. Pat. No. 7,105,724 |
| | U.S. Pat. No. 5,670,454 |
| | U.S. Pat. No. 7,105,724 |
| | U.S. Pat. No. 7,105,724 |
| | U.S. Pat. No. 7,105,724 |
| | U.S. Pat. No. 7,105,724 |
| | U.S. Pat. No. 5,670,454 |
| | U.S. Pat. No. 7,105,724 |
| | U.S. Pat. No. 7,105,724 |
| | U.S. Pat. No. 7,105,724 |
| | U.S. Pat. No. 5,670,454 |
| | U.S. Pat. No. 7,105,724 |
| | U.S. Pat. No. 7,105,724 |
| | U.S. Pat. No. 7,105,724 |
| | U.S. Pat. No. 7,105,724 |
| | U.S. Pat. No. 7,105,724 |
| | U.S. Pat. No. 6,153,401 |
| | U.S. Pat. No. 6,100,446 |
| | WO 2005/107437 |
| | U.S. Pat. No. 5,670,454 |
| | U.S. Pat. No. 5,608,147 |
| | U.S. Pat. No. 5,670,454 |
| | WO 2004/055191 |
| | WO 199638567 |
| | U.S. Pat. No. 6,791,014 |
| | US 2002/0073443, |
| | US 20080052798 |
| | WO2011/022470 |
| | WO2011/034936 |
| | WO2011/028832 |
| | WO2011/028833 |
| | WO2011/028836 |
| | WO2011/068567 |
| | WO2011/076345 |
| | WO2011/085221 |
| | WO2011/094199 |
| | WO2011/094205 |
| | WO2011/068567 |
| | WO2011/085221 |
| | WO2011/094199 |
| | WO2011/094205 |
| | WO2011/145015 |
| | WO2012047595 |
| | WO2012048124 |
| | WO2012048136 |
| | WO2012048807 |
| | WO2012049663 |
| | WO2012050962 |
| | WO2012056401 |
| | WO2012057466 |
| | WO2012057465 |
| | WO2012058223 |
| plant metabolism | WO2011/060920 |
| | WO2011/119115 |
| | WO2011/102394 |
| reproduction | WO2011/113839 |
| Biofuels | WO2012073493 |

Additional agronomic traits of interest include the following:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al. Cell 78:1089 (1994) (Arabidopsis RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt .delta.-endotoxin gene. Moreover, DNA molecules encoding .delta.-endotoxin genes can be purchased from American Type Culture Collection, Manassas, Va., for example, under ATCC Accession Nos. 40098, 67136, 31995 and 31998.

D. A lectin. See, for example, Van Damme et al., Plant Molec. Biol. 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* .alpha.-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776, which discloses peptide derivatives of tachyplesin which inhibit fungal plant pathogens, and PCT application WO 95/18855 which teaches synthetic antimicrobial peptides that confer disease resistance.

N. A membrane permease, a channel former or a channel blocker. For example, see the disclosure of Jaynes et al., Plant Sci 89:43 (1993), of heterologous expression of a cecropin-.beta. lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-.alpha.-1,4-D-polygalacturonases facilitate fungal colonization and plant nutrient release by solubilizing plant cell wall homo-.alpha.-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., Current Biology, 5(2) (1995).

U. Antifungal genes. See Cornelissen and Melchers, Plant Physiol., 101:709-712 (1993); Parijs et al., Planta 183:258-264 (1991) and Bushnell et al., Can. J. of Plant Path. 20(2):137-149 (1998).

V. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

F. Genes that confer resistance to HPPD inhibitors, such as an N-(tetrazol-4-yl)- or N-(triazol-3-yl)arylcarboxamide, an N-(1,2,5-oxadiazol-3-yl)benzamide, tembotrione, sulcotrione, topramezone, bicyclopyrone, tefuryltrione, isoxaflutole, pyrasulfotole, and mesotrione.

3. Genes that Confer or Contribute to a Value-Added Trait, such as:

A. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

B. Decreased phytate content—1) Introduction of a phytase-encoding gene enhances breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. This could be accomplished by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* .alpha.-amylase), Elliot et al., Plant Molec. Biol. 21:515 (1993) (nucleotide sequences of tomato invertase genes), SOgaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Soybean Transformation

Numerous methods for plant transformation have been developed including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra and Moloney et al., Plant Cell Reports 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4.mu.m. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987); Sanford, J. C., Trends Biotech. 6:299 (1988); Klein et al., Bio/Tech. 6:559-563 (1988); Sanford, J. C. Physiol Plant 7:206 (1990); Klein et al., Biotechnology 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J., 4:2731 (1985); Christou et al., Proc Natl. Acad. Sci. USA 84:3962 (1987). Direct uptake of DNA into protoplasts using $CaCl_2$ precipitation, polyvinyl alcohol or poly-L-ornithine has also been reported. Hain et al., Mol. Gen. Genet 199:161 (1985) and Draper et al., Plant Cell Physiol. 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994)).

Following transformation of soybean target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular soybean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Single-Gene Conversions

When the term "soybean plant" is used in the context of the present invention, this also includes any single gene conversions of that variety. The term single gene converted plant as used herein refers to those soybean plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9 or more times to the recurrent parent. The parental soybean plant that contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcros sing techniques. Single gene traits may or may not be transgenic; examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445; the disclosures of which are specifically hereby incorporated by reference.

Tissue Culture

Further reproduction of the variety can occur by tissue culture and regeneration. Tissue culture of various tissues of soybeans and regeneration of plants therefrom is well known and widely published. For example, reference may be had to Komatsuda, T. et al., Crop Sci. 31:333-337 (1991); Stephens, P. A., et al., Theor. Appl. Genet. (1991) 82:633-635; Komatsuda, T. et al., Plant Cell, Tissue and Organ Culture, 28:103-113 (1992); Dhir, S. et al., Plant Cell Reports (1992) 11:285-289; Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce soybean plants having all the physiological and morphological characteristics of soybean variety DLL1273.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a soybean plant by crossing a first parent soybean plant with a second parent soybean plant wherein the first or second parent soybean plant is a soybean plant of soybean variety DLL1273. Further, both first and second parent soybean plants can come from the soybean variety DLL1273. Thus, any such methods using soybean variety DLL1273 are part of this invention: selfing, backcrosses, hybrid production, crosses to populations, and the like. All plants produced using soybean variety DLL1273 as at least one parent are within the scope of this invention, including those developed from varietys derived from soybean variety DLL1273. Advantageously, the soybean variety could be used in crosses with other, different, soybean plants to produce the first generation (F1) soybean hybrid seeds and plants with superior characteristics. The variety of the invention can also be used for transformation where exogenous genes are introduced and expressed by the variety of the invention. Genetic variants created either through traditional breeding methods using soybean variety DLL1273 or through transformation of soybean variety DLL1273 by any of a number of protocols known to those of skill in the art are intended to be within the scope of this invention.

The following describes breeding methods that may be used with soybean variety DLL1273 in the development of further soybean plants. One such embodiment is a method for developing a soybean variety DLL1273 progeny soybean plant in a soybean plant breeding program comprising: obtaining the soybean plant, or a part thereof, of variety DLL1273 utilizing said plant or plant part as a source of breeding material and selecting a soybean variety DLL1273 progeny plant with molecular markers in common with variety DLL1273 and/or with morphological and/or physiological characteristics selected from the characteristics listed in Table 1. Breeding steps that may be used in the soybean plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of soybean variety DLL1273 progeny soybean plants, comprising crossing variety DLL1273 with another soybean plant, thereby producing a population of soybean plants, which, on average, derive 50% of their alleles from soybean variety DLL1273. A plant of this population may be selected and repeatedly selfed or sibbed with a soybean variety resulting from these successive filial generations. One embodiment of this invention is the soybean variety produced by this method and that has obtained at least 50% of its alleles from soybean variety DLL1273.

One of ordinary skill in the art of plant breeding would know how to evaluate the traits of two varietys to determine if there is no significant difference between the two traits expressed by those varietys. For example, see Fehr and Walt, Principles of Variety Development, p 261-286 (1987). Thus the invention includes soybean variety DLL1273 progeny soybean plants comprising a combination of at least two variety DLL1273 traits selected from the group consisting of those listed in Table 1 or the variety DLL1273 combination of traits listed in the Summary of the Invention, so that said progeny soybean plant is not significantly different for said traits than soybean variety DLL1273 as determined at the 5% significance level when grown in the same environmental conditions. Using techniques described herein, molecular markers may be used to identify said progeny plant as a soybean variety DLL1273 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of soybean variety DLL1273 may also be characterized through their filial relationship with soybean variety DLL1273, as for example, being within a certain number of breeding crosses of soybean variety DLL1273. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean variety DLL1273 and its progeny. For example, progeny produced by the methods described herein may be within 1, 2, 3, 4 or 5 breeding crosses of soybean variety DLL1273.

As used herein, the term "plant" includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, cotyledons, hypocotyls, stems, pistils, petiole, and the like.

Industrial Uses

The seed of soybean variety DLL1273, the plant produced from the seed, the hybrid soybean plant produced from the crossing of the variety with any other soybean plant, hybrid seed, and various parts of the hybrid soybean plant can be utilized for human food, livestock feed, and as a raw material in industry.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board and American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics, lubricants and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthier, less expensive replacement for animal protein in meats as well as in dairy-type products.

Deposit Information

Applicant made a deposit of at least 2500 seeds of soybean variety DLL1273 disclosed herein with the American Tyoe Culture Collection (ATCC), 10801 University Blvd, Manassas, Va. under Accession No. PTA-121587. Seed of the soybean variety DLL1273 is located at 210 Drier Road, De Witt, Ark. 72042. The lot number for this seed material is DLL1273_DW2012. The seeds were deposited with the ATCC on Sep. 9, 2014. Access to this deposit will be available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer, and will be replaced if it becomes nonviable during that period. Applicant does not waive any rights granted under this patent or under the Plant Variety Protection Act (7 U.S.C. 2321 et seq.).

Definitions

In the description and tables which follow, a number of terms are used. In order to provide a clear and consistent understanding of the specification and claims, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Appearance. A visual observation rating based on a scale of 1-9 as to the varieties overall appearance as far as adaptability, plant height, lodging, plant health, etc., at the time of rating as one would want it to look to be an excellent variety. A value of 1 indicates a very poor and not adapted variety while a value of 9 indicates a very nice, awesome looking variety with a lot of pods and perceived yield from a visual observation.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bacterial Pustule: Rated on a scale from 1 to 9 with 1 indicating no bacterial pustule found in the rated plot and a value of 9 indicating all plants with infection by bacterial Pustule in the rated plot.

Brown Stem Rot. This is a visual disease score from 1 to 9 comparing all genotypes in a given test. The score is based on leaf symptoms of yellowing and necrosis caused by brown stem rot. Visual scores range from a score of 9, which indicates no symptoms, to a score of 1 which indicates severe symptoms of leaf yellowing and necrosis.

Cotyledon. A cotyledon is a type of seed leaf. The cotyledon contains the food storage tissues of the seed.

Embryo. The embryo is the small plant contained within a mature seed.

Emergence. This score indicates the ability of the seed to emerge when planted 3" deep in sand at a controlled temperature of 25 .degree. C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

Frogeye Leaf Spot (fels). Primarily a foliar disease of soybean caused by the fungus *Cercospora sojina*. Lesions on leaves are circular to angular spots which vary in size (less than 1 mm to 5 mm in diameter). The lesions are gray to brown spots surrounded by a narrow red or dark reddish-brown margin. The disease can be seedborne. The rating scale is from 1 to 9 with 1 indicating no Frogeye present and 9 indicating the leaf is entirely covered and the leaves are dropping off the plant (and pods also), very bad.

Hilum. This refers to the scar left on the seed that marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Iron Chlorosis on Calcareous Soil. When conducting a test for salt or uptake of salt, there are three reactions: a) Excluder: The plant takes up the salt but it is not translocated up through the plant to the leaves and the plant will survive normally in the presence of high salt in the soil. b) Includer: The plants translocate the salt up through the vascular pathways to the leaves resulting in scorching of the leaves and later death and defoliation. c) Segregater: Some plants are Excluders and some plants are Includers. This variety segregates for the charater.

Iron-Deficiency Chlorosis. Plants are scored 1 to 9 based on visual observations. A score of 9 means no stunting of the plants or yellowing of the leaves and a score of 1 indicates the plants are dead or dying caused by iron-deficiency chlorosis, a score of 5 means plants have intermediate health with some leaf yellowing.

Lodging Resistance. Lodging is rated on a scale of 1 to 5. A score of 1 indicates that almost all plants are erect and standing up. A score of 2 indicates all plants are leaning slightly or a few plants are lying on the ground. A score of 3 indicates all plants leaning moderately and/or several plants lying on the ground. A score of 4 indicates all plants leaning considerably and/or a lot of plants lying on the ground and a score of 5 indicates all plants lying on the ground.

Maturity Date. Plants are considered mature when 95% of the pods have reached their mature color. The number of days are calculated from the planting date.

Maturity Group. This refers to an agreed-on industry division of groups of varieties based on zones in which they are adapted, primarily according to day length or latitude. They consist of very long day length varieties (Groups 000, 00, 0), and extend to very short day length varieties (Groups VII, VIII, IX, X).

Multi-yield. Average yield across all the locations of the varieties in the trial.

Relative Maturity (RM). The term relative maturity is a numerical value that is assigned to a soybean variety based on comparisons with the maturity values of other varieties. The number preceding the decimal point in the RM refers to the maturity group. The number following the decimal point refers to the relative earliness or lateness within each maturity group. For example, a 3.0 is an early group III variety, while a 3.9 is a late group III variety.

Oil or oil percent. Soybean seeds contain a considerable amount of oil. Oil is measured by NIR spectrophotometry, and is reported on an as is percentage basis.

Oleic Acid Percent. Oleic acid is one of the five most abundant fatty acids in soybean seeds. It is measured by gas chromatography and is reported as a percent of the total oil content.

Palmitic Acid Percent. Palmitic acid is one of the five most abundant fatty acids in soybean seeds. It is measured by gas chromatography and is reported as a percent of the total oil content.

*Phytophthora* Root Rot (Prr). *Phytophthora* root rot is rated on a scale of 0 to 9, with a score of 0 being the best or highest tolerance (no dead plants) ranging to a score of 9 which indicates the plants have no tolerance to *Phytophthora* and are dead.

Phenotypic Score. The Phenotypic Score is a visual rating of general appearance of the variety. All visual traits are considered in the score including healthiness, standability, appearance and freedom from disease. Ratings are scored from 1 being poor to 9 being excellent.

Plant Height. Average length in inches of mature plants from the ground to the tip of the main stem.

Pod. This refers to the fruit of a soybean plant. It consists of the hull or shell (pericarp) and the soybean seeds.

Pod and Stem Blight. Also known as *Diaporthe phaseolorum* var. *sojae*. Pod and Stem Blight results in poor seed quality and has symptoms of an arrangement of black fruiting structures in linear rows on the stems. Infected seeds crack and shrivel and are often covered with white mold. These seeds fail to germinate, or produce weak seedlings with brownish-red pinpoint lesions on the cotyledons.

Protein Percent. Soybean seeds contain a considerable amount of protein. Protein is generally measured by NIR spectrophotometry and is reported on an as is percentage basis.

Pubescence. This refers to a covering of very fine hairs closely arranged on the leaves, stems and pods of the soybean plant.

Purple Seed Stain. Also known as *Cercospora* kikuchii. A fungus that causes a pink or light to dark purple discoloration of the mature seed coat. The size of the discoloration may vary from a small spot to the entire seed surface. Affected seed may be cracked, rough and dull.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seed Protein Peroxidase Activity. Seed protein peroxidase activity refers to a chemical taxonomic technique to separate varieties based on the presence or absence of the peroxidase enzyme in the seed coat. There are two types of soybean varieties: those having high peroxidase activity (dark red color) and those having low peroxidase activity (no color).

Seed Yield (Bushels/Acre). The yield in bushels/acre is the actual yield of the grain at harvest.

Seeds per Pound. Soybean seeds vary in seed size, therefore, the number of seeds required to make up one pound also varies. This affects the pounds of seed required to plant a given area and can also impact end uses.

Shattering. The amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground and a score of 1 indicates 100% of the pods are opened.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Southern Root Knot Nematode. Also known as *Meloidogyne incognita*. One of the most common nematode pest of soybeans in the southern states. Symptoms include severe stunting and formation of galls or knots on the roots. Also, plants may appear to suffer nutrient deficiencies and may wilt during hot periods of the day. Nematode damage reduces yield and lowers quality.

Soybean Mosaic Virus. Soybean mosaic virus is the most widely distributed virus diseases of soybeans. The leaves of infected plants are distorted and narrower than normal, and develop dark green swellings along the veins. Infected leaflets are puckered and curl down at the margin. Plants infected warly in the season are stunted, with shortened petioles and internodes. Diseased seed pods are often smaller, flattened, less pubescence, and curved more acutely than pods of healthy plants. In addition, infected seed are mottled brown or black, usually smaller than seeds from healthy plants, and germination may be reduced.

Stem Canker (sc). Caused by *D. phaseolorum* var. *meridionalis*. The first symptoms occur during the early reproductive stages as small, reddish brown lesions, usually near a lower leaf node. As the season progresses, the lesions expand longitudinally to form cankers which are slightly sunken. The stem lesions become long and the leaf symptoms develop with characteristic interveinal chlorosis and necrosis, but no wilting. Foliar symptoms and plant death are caused in part by a phytotoxin. Rated "resistant" or "susceptible" if from disease in nursery. If from field observations it is rated on a scale from 0 to 9, where a value of 0 indicates no stem canker and a value of 9 indicates plants are dead.

Sudden Death Syndrome (sds). Caused by the soilborne fungus, *Fusarium solani* f. sp. *glycines*. The symptoms first appear on leaves as scattered, interveinal chlorotic spots, which may become necrotic or enlarge and form streaks. Leaflets detach from the petioles. The root-mass of infected plants are reduced and discolored and precede foliar symptoms. The infected plants often have increased flower and pod abortion and reduced seed size. Rated on a scale from 1 to 9 with 1 indicating no symptoms and 9 indicating plants dying or dead.

Virus. Rated on a scale from 1 to 9 with 1 indicating no virus noted or found in the plot rated and 9 indicating all plants affected in the plot rated.

Wildfire. A type of bacterial leaf blight also known as *Pseudomonas tabaci*. The symptoms of Wildfire include light brown spots of variable size and shape, which are surrounded by a broad yellow halo. Smaller dark brown to black lesions sometimes form without the halo. During wet weather, the lesions expand to form large dead areas that eventually tear away resulting in a tattered appearance.

That which is claimed:

1. A seed of soybean variety DLL1273, representative sample seed of said variety is deposited under ATCC Accession No. PTA-121587.

2. A soybean plant, or a part thereof, produced by growing the seed of claim 1.

3. A tissue culture produced from protoplasts or cells from the plant of claim 2, wherein said cells or protoplasts are produced from a plant part selected from the group consisting of leaf, pollen, ovule, embryo, cotyledon, hypocotyl, meristematic cell, root, root tip, pistil, anther, flower, seed, shoot, stem, pod and petiole.

4. A soybean plant regenerated from the tissue culture of claim 3, wherein said soybean plant has all of the physiological and morphological characteristics of the plant of claim 2.

5. A method for producing a soybean seed, comprising crossing two soybean plants and harvesting the resultant soybean seed, wherein at least one soybean plant is the soybean plant of claim 2.

6. A soybean seed produced by the method of claim 5.

7. A soybean plant, or a part thereof, produced by growing said seed of claim 6.

8. The method of claim 5, wherein at least one of said soybean plants further comprises at least one transgene.

9. A method of producing an herbicide resistant soybean plant, wherein said method comprises introducing a gene conferring herbicide resistance into the plant of claim 2.

10. A herbicide resistant soybean plant produced by the method of claim 9, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, benzonitrile, an N-(tetrazol-4-yl)- or N-(triazol-3-yl)arylcarboxamide, an N-(1,2,5-oxadiazol-3-yl)benzamide, tembotrione, sulcotrione, topramezone, bicyclopyrone, tefuryltrione, isoxaflutole, pyrasulfotole, and mesotrione.

11. A method of producing a pest or insect resistant soybean plant, wherein said method comprises introducing a gene conferring pest or insect resistance into the soybean plant of claim 2.

12. A pest or insect resistant soybean plant produced by the method of claim 11.

13. The soybean plant of claim 12, wherein the gene encodes a Bacillus thuringiensis (Bt) endotoxin.

14. A method of producing a disease resistant soybean plant, wherein said method comprises introducing a gene which confers disease resistance into the soybean plant of claim 2.

15. A disease resistant soybean plant produced by the method of claim 14.

16. A method of producing a soybean plant with modified fatty acid metabolism or modified carbohydrate metabolism, wherein the method comprises introducing a gene encoding a protein selected from the group consisting of phytase, fructosyltransferase, levansucrase, α-amylase, invertase and starch branching enzyme or encoding an antisense of stearyl-ACP desaturase into the soybean plant of claim 2.

17. A soybean plant having modified fatty acid metabolism or modified carbohydrate metabolism produced by the method of claim 16.

18. A method of introducing a desired trait into soybean variety DLL1273, wherein the method comprises:
   (a) crossing a DLL1273 plant, wherein a representative sample of seed is deposited under ATCC Accession No. PTA-121587, with a plant of another soybean variety that comprises a desired trait to produce progeny plants wherein the desired trait is selected from the group consisting of male sterility, herbicide resistance, insect resistance, modified fatty acid metabolism, modified carbohydrate metabolism, modified seed yield, modified oil percent, modified protein percent, modified lodging resistance, modified shattering, modified iron-deficiency chlorosis and resistance to bacterial disease, fungal disease or viral disease;
   (b) selecting one or more progeny plants that have the desired trait to produce selected progeny plants;
   (c) crossing the selected progeny plants with the DLL1273 plant to produce backcross progeny plants;
   (d) selecting for backcross progeny plants that have the desired trait and all of the physiological and morphological characteristics of soybean variety DLL1273 listed in Table 1; and
   (e) repeating steps (c) and (d) two or more times in succession to produce selected third or higher backcross progeny plants that comprise the desired trait and all of the physiological and morphological characteristics of soybean variety DLL1273 listed in Table 1.

19. A soybean plant produced by the method of claim 18, wherein the plant has the desired trait.

20. The soybean plant of claim 19, wherein the desired trait is herbicide resistance and the resistance is conferred to an herbicide selected from the group consisting of glyphosate, sulfonylurea, imidazolinone, dicamba, glufosinate, phenoxy proprionic acid, L-phosphinothricin, cyclohexone, cyclohexanedione, triazine, benzonitrile, an N-(tetrazol-4-yl)- or N-(triazol-3-yl)arylcarboxamide, an N-(1,2,5-oxadiazol-3-yl)benzamide, tembotrione, sulcotrione, topramezone, bicyclopyrone, tefuryltrione, isoxaflutole, pyrasulfotole, and mesotrione.

21. The soybean plant of claim 19, wherein the desired trait is insect resistance and the insect resistance is conferred by a gene encoding a Bacillus thuringiensis endotoxin.

22. The soybean plant of claim 19, wherein the desired trait is modified fatty acid metabolism or modified carbohydrate metabolism and said desired trait is conferred by a nucleic acid encoding a protein selected from the group consisting of phytase, fructosyltransferase, levansucrase, α-amylase, invertase and starch branching enzyme or encoding an antisense of stearyl-ACP desaturase.

23. A method of producing a commodity plant product, comprising obtaining the plant of claim 2, or a part thereof, wherein the commodity plant product is protein concentrate, protein isolate, soybean hulls, meal, flour, or oil and producing said commodity plant product therefrom.

24. A plant, or a part thereof, obtained by vegetative reproduction from the plant, or a part thereof, of claim 2, said plant, or a part thereof, expressing all the physiological and morphological characteristics of soybean variety DLL1273.

25. A plant, or a part thereof, obtained by vegetative reproduction from the plant, or a part thereof, of claim 7, said plant, or a part thereof, expressing all the physiological and morphological characteristics of soybean variety DLL1273.

* * * * *